United States Patent [19]

Linder

[11] Patent Number: 4,988,789

[45] Date of Patent: Jan. 29, 1991

[54] PROCESS FOR PREPARING GLYCINE HYDROCHLORIDE

[75] Inventor: Jerome Linder, Westfield, N.J.

[73] Assignee: Sandoz Ltd., Basel, Switzerland

[21] Appl. No.: 461,157

[22] Filed: Jan. 5, 1990

[51] Int. Cl.$^5$ .............................................. C07C 227/00
[52] U.S. Cl. .................................................... 562/575
[58] Field of Search ......................................... 562/575

[56] References Cited

U.S. PATENT DOCUMENTS 4,234,744 11/1980 Effenberger et al. ............... 562/575

FOREIGN PATENT DOCUMENTS 61-243050 10/1986 Japan .................................. 562/575

OTHER PUBLICATIONS

DiBlosio et al. Chem. Abst., vol. 88, #62606c(1978).
Limanov et al. Chem. Abst., vol. 102, #113,909w.

Primary Examiner—James H. Reamer
Attorney, Agent, or Firm—Gerald D. Sharkin; Robert S. Honor; Joseph J. Borovian

[57] ABSTRACT

An improved process for preparing glycine hydrochloride in a high purity and high yield employing water as the solvent.

22 Claims, No Drawings

PROCESS FOR PREPARING GLYCINE HYDROCHLORIDE

The present invention relates to an improved process for preparing glycine hydrochloride in a high purity and high yield employing water as the solvent.

Glycine hydrochloride is known and, in fact, it has just recently been approved by the FDA as a nutrient food additive. Although its inclusion in a number of foods and pharmaceuticals has been explored in the past, the use of glycine hydrochloride as an inactive excipient is expected to increase appreciably now that it has gained FDA approval. Unfortunately, however, there is no available commercial source that can provide glycine hydrochloride in either the purity or bulk that would be especially suitable for this purpose. To this end, the instant invention is directed to a simple and economic process for preparing glycine hydrochloride in a high purity and high yield employing the ideal solvent, water.

In accordance with the process of the instant invention, glycine hydrochloride is prepared by a two-step process comprising: (1) in a first step, adding glycine to concentrated hydrochloric acid, heating the mixture, cooling the resultant solution, and filtering the resultant solid to obtain a first crop of the desired product; and 2) in a second step, cooling the aqueous filtrate from the first step, adding anhydrous hydrogen chloride to the cooled filtrate, allowing the mixture to warm to room temperature, cooling the mixture, and filtering the resultant solid to obtain a second crop of the desired product. The combined crops result in the obtainment of the desired glycine hydrochloride in a high purity and high yield.

In the first step of the process, i.e., in preparing the first crop of the desired product, the reactants are combined in an approximately equimolar amount, or one of the reactants may be present in a slightly molar excess, and the reaction mixture is heated to between 45° and 60° C., preferably between 50° and 55° C. The resultant solution is then cooled to between −20° and 5° C., preferably between -15° and 0° C., and maintained at that temperature for a period of between 10 minutes and 30 minutes. The resultant solid is then filtered to obtain a first crop of the desired product in a yield of between 65% and 70%.

In the second step of the process, i.e., in preparing the second crop of the desired product, the filtrate resulting from the first step is cooled to between −10° and 10° C., preferably between −5° and 5° C., and to the cooled filtrate is added a molor excess of anhydrous hydrogen chloride, at which time precipitation commences and the temperature begins to rise. The reaction mixture is allowed to warm to about 25° C. and maintained at that temperature for between 10 and 30 minutes, after which time it is cooled to between −25° and 0° C., preferably between −20° and −10° C., and maintained at that temperature for a period of between 10 and 20 minutes. The resultant solid is then filtered to obtain a second crop of the desired product in a yield of between 20% and 25%.

The first and second crops are then combined to obtain the desired glycine hydrochloride in a purity of at least 95% and a yield of at least 90%.

The following example is for the purpose of illustration only and is not intended in any way to limit the scope of the instant invention.

EXAMPLE (a) 100g (1.33 moles) of glycine are added to 150 ml. (1.27 moles) of concentrated hydrochloric acid and the reaction mixture is heated to between 50° and 53° C. The resultant solution is then cooled to between −10° and −8° C. and maintained at that temperature for between 15 and 20 minutes.

The resultant solid is then filtered, the filtrate is cooled to −15° C. and maintained at this temperature for about 10 minutes, and then filtered through the same filter. The residue is then dried in a vacuum oven for 18 hours at 90° C. to yield 94g of a first crop of glycine hydrochloride.

(b) The filtrate from a) above is cooled to 0° C. and to the cooled filtrate is added 60g (1.64 moles) of anhydrous hydrogen chloride, at which time precipitation commences and the temperature of the mixture begins to rise. The reaction mixture is allowed to warm to 23° C. and maintained at this temperature for about 15 minutes. The mixture is then cooled to −15° C. and maintained at this temperature for between 10 and 15 minutes. The resultant solid is then filtered and the residue is dried in a vacuum oven for 18 hours at 90° C. to yield 42g of a second crop of glycine hydrochloride.

The first and second crops are combined to obtain the desired glycine hydrochloride in a purity of 99% and a yield of 91.4%.

What is claimed is:

1. A process for preparing glycine hydrochloride comprising: (1) in a first step, adding glycine to concentrated hydrochloric acid, heating the mixture, cooling the resultant solution, and filtering the resultant solid to obtain a first crop of glycine hydrochloride; and (2) in a second step, cooling the aqueous filtrate from the first step, adding a molar excess of anhydrous hydrogen chloride to the cooled filtrate, allowing the mixture to warm to room temperature, cooling the mixture, and filtering the resultant solid to obtain a second crop of glycine hydrochloride.

2. A process according to claim 1 wherein, in the first step, the glycine and the concentrated hydrochloric acid are combined in an equimolar amount, or in a slightly molar excess of one of said reactants.

3. A process according to claim 1 wherein, in the first step, the glycine and the concentrated hydrochloric acid are heated to between 45° and 60° C.

4. A process according to claim 3 wherein the glycine and the concentrated hydrochloric acid are heated to between 50° and 55° C.

5. A process according to claim 1 wherein, in the first step, the resultant solution is cooled to between −20° and 5° C.

6. A process according to claim 5 wherein the resultant solution is cooled to between −15° and 0° C.

7. A process according to claim 5 wherein the temperature is maintained for a period of between 10 minutes and 30 minutes.

8. A process according to claim 1 wherein, in the second step, the aqueous filtrate is cooled to between −10° and 10° C 9. A process according to claim 8 wherein the aqueous filtrate is cooled to between −5° and 5° C.

10. A process according to claim 1 wherein, in the second step, the mixture is maintained at room temperature for a period of between 10 minutes and 30 minutes.

11. A process according to claim 1 wherein, in the second step, the mixture is cooled to between −25° and 0° C.

12. A process according to claim 11 wherein the mixture is cooled to between −20° and −10° C.

13. A process according to claim 11 wherein the temperature is maintained for a period of between 10 and 20 minutes.

14. A process for preparing glycine hydrochloride comprising: 1) in a first step, adding glycine to concentrated hydrochloric acid in an equimolar amount or in a slightly molar excess of one of said reactants, heating the mixture to between 45° and 60° C., cooling the resultant solution to between −20° and 5° C., and filtering the resultant solid to obtain a first crop of glycine hydrochloride; and (2) in a second step, cooling the aqueous filtrate from the first step to between −10° and 10° C., adding a molar excess of anhydrous hydrogen chloride to the cooled filtrate, allowing the mixture to warm to room temperature, cooling the mixture to between −25° and 0° C., and filtering the resultant solid to obtain a second crop of glycine hydrochloride.

15. A process according to claim 14 wherein, in the first step, the glycine and the concentrated hydrochloric acid are heated to between 50° and 55° C.

16. A process according to claim 14 wherein, in the first step, the resultant solution is cooled to between −15° and 0° C.

17. A process according to claim 16 wherein the temperature is maintained for a period of between 10 minutes and 30 minutes.

18. A process according to claim 14 wherein, in the second step, the aqueous filtrate is cooled to between −5° and 5° C.

19. A process according to claim 14 wherein, in the second step, the mixture is maintained at room temperature for a period of between 10 minutes and 30 minutes.

20. A process according to claim 14 wherein, in the second step, the mixture is cooled to between −20° and −10° C.

21. A process according to claim 20 wherein the temperature is maintained for a period of between 10 and 20 minutes.

22. A process for preparing glycine hydrochloride comprising: 1) in a first step, adding glycine to concentrated hydrochloric acid in an equimolar amount or in a slightly molar excess of one of said reactants, heating the mixture to between 50° and 55° C., cooling the resultant solution to between −15° and 0° C. and maintaining this temperature for a period of between 10 minutes and 30 minutes, and filtering the resultant solid to obtain a first crop of glycine hydrochloride; and 2) in a second step, cooling the aqueous filtrate from the first step to between −5° and 5° C., adding a molar excess of anhydrous hydrogen chloride to the cooled filtrate, allowing the mixture to warm to room temperature and maintaining this temperature for a period of between 10 minutes and 30 minutes, cooling the mixture to between −20° and −10° C. and maintaining this temperature for a period of between 10 and 20 minutes, and filtering the resultant solid to obtain a second crop of glycine hydrochloride.

* * * * *